(12) United States Patent
Bungartz et al.

(10) Patent No.: US 7,948,362 B2
(45) Date of Patent: May 24, 2011

(54) IMPLANTABLE MEDICAL TRANSCEIVER DEVICE

(75) Inventors: Joern Bungartz, Berlin (DE); Joachim Reinke, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 1000 days.

(21) Appl. No.: 11/769,668

(22) Filed: Jun. 27, 2007

(65) Prior Publication Data
US 2008/0048836 A1 Feb. 28, 2008

(30) Foreign Application Priority Data

Aug. 22, 2006 (DE) .......................... 10 2006 039 345

(51) Int. Cl.
*H04Q 5/22* (2006.01)
*G08B 13/14* (2006.01)
*H04B 1/00* (2006.01)
*H04B 1/10* (2006.01)
*A61N 1/00* (2006.01)
*A61B 5/00* (2006.01)

(52) U.S. Cl. .................. 340/10.33; 340/10.1; 340/10.41; 340/572.1; 340/572.2; 455/63.3; 455/703; 455/3.02; 455/427; 607/30; 600/300

(58) Field of Classification Search ........................ None
See application file for complete search history.

(56) References Cited

U.S. PATENT DOCUMENTS

| | | | | |
|---|---|---|---|---|
| 5,307,349 A * | 4/1994 | Shloss et al. | .................. | 370/442 |
| 7,050,775 B2 * | 5/2006 | Mayor et al. | .................. | 455/258 |
| 7,079,009 B2 * | 7/2006 | Gallagher et al. | ........... | 340/10.2 |
| 7,212,126 B2 * | 5/2007 | Hachiga | ..................... | 340/572.8 |
| 7,239,963 B2 * | 7/2007 | Suzuki | .......................... | 701/211 |
| 7,626,488 B2 * | 12/2009 | Armstrong et al. | .......... | 340/10.2 |
| 7,683,761 B2 * | 3/2010 | Burghard et al. | ............ | 340/10.2 |
| 2001/0041551 A1 | 11/2001 | Rotzoll | | |

(Continued)

FOREIGN PATENT DOCUMENTS

EP 1 353 447 10/2003

(Continued)

OTHER PUBLICATIONS

German Search Report, dated Jul. 15, 2009.

(Continued)

*Primary Examiner* — Davetta W Goins
*Assistant Examiner* — Fekadeselassie Girma
(74) *Attorney, Agent, or Firm* — ARC IP Law, PC; Joseph J. Mayo

(57) ABSTRACT

An implantable medical device having a transceiver for transmitting/receiving wirelessly transmitted data, which is turned off or switched into an energy-saving rest state between individual data transmissions via the transceiver and having a waking unit which is implemented to switch the transceiver by a waking signal from its turned-off state or its rest state into its fully operational state, the waking unit having a low-power receiver and a waking control unit of which the low-power receiver is implemented to monitor multiple predefined frequency ranges in such a way that in case of a transmission of sufficient signal strength in one of the frequency ranges, it generates an output signal and outputs it to the waking control unit and of which the waking control unit is implemented to analyze output signals of the low-power receiver and output a waking signal to the transceiver which switches it on or to fully operational.

11 Claims, 3 Drawing Sheets

U.S. PATENT DOCUMENTS

| | | | |
|---|---|---|---|
| 2003/0014186 A1* | 1/2003 | Adams et al. | 701/207 |
| 2003/0119568 A1 | 6/2003 | Menard | |
| 2005/0288738 A1* | 12/2005 | Bange et al. | 607/60 |
| 2006/0059049 A1* | 3/2006 | Morris et al. | 705/26 |
| 2006/0122667 A1* | 6/2006 | Chavan et al. | 607/60 |
| 2006/0129308 A1* | 6/2006 | Kates | 701/200 |
| 2009/0046763 A1* | 2/2009 | Kerai | 375/136 |

FOREIGN PATENT DOCUMENTS

| | | |
|---|---|---|
| WO | WO 2005/062644 | 7/2005 |
| WO | WO 2005/099817 | 10/2005 |

OTHER PUBLICATIONS

German Search Report, dated Apr. 12, 2007.

* cited by examiner

IMPLANTABLE MEDICAL TRANSCEIVER DEVICE

This application takes priority from German Patent Application DE 10 2006 039 345.7 filed 22 Aug. 2006, the specification of which is hereby incorporated herein by reference.

BACKGROUND OF THE INVENTION

1. Field of the Invention

The present invention relates to an implantable medical device having an installed transceiver for wirelessly transmitting and receiving data, which may be turned off between individual data transmissions.

2. Description of the Related Art

Such implantable medical devices may be cardiac pacemakers or cardioverters/defibrillators or combinations of the two, for example. In the meantime, multiple such implants have become known, which have a transceiver, with the aid of which it is possible to transmit physiological or technical data or both from the implant to an external device or vice versa, with the aid of an external device, to transmit data to the implant. The latter may be desirable for programming the implant or also for querying specific data, for example.

The problem basically always exists in such implants that the energy resources of the implant are limited and are usually provided by a battery permanently installed in the implant. Therefore, the object basically exists of restricting the energy consumption of the implant as much as possible. This may be performed, for example, by turning off components of the implant which are currently not needed. The further problem arises in this case of how these implant parts are to be turned back on.

In addition, it is to be taken into consideration that possibly multiple implants are mutually in range or are in range of one or more external devices.

BRIEF SUMMARY OF THE INVENTION

The object of the present invention is to provide an implant which is suitable for the above-mentioned scenario and is as energy-saving as possible.

This object is achieved according to the present invention by an implant of the type cited at the beginning which, in addition to the transceiver, has a waking unit, which is implemented to switch the transceiver from its rest state or from its turned-off state, in which it requires little or no energy, into its fully operational state, in which it accordingly requires more energy. For this purpose, the waking unit has a second, separate low-power receiver, which has a significantly lower energy demand than the transceiver in its turned-on or fully operational state. In addition, the waking unit has a waking control unit, which is connected to an output of the low-power receiver. The low-power receiver is implemented to monitor multiple predefined frequency ranges in such a way that in case of a transmission of sufficient signal strength in one or more of the frequency ranges, it generates an output signal and outputs it to the waking control unit. The waking control unit is implemented to analyze output signals of the low-power receiver and output a waking signal to the transceiver, which switches it on or to fully operational if a predefined condition is met or multiple predefined conditions are met. The waking control unit is implemented in such a way that it outputs a waking signal to the transceiver if the low-power receiver outputs a sequence of output signals which identify that the low-power receiver has detected a sequence of transmissions of sufficient signal strength in various frequency ranges, which correspond to a predefined series or sequence. If the frequency ranges monitored by the low-power receiver are the frequency ranges A, B, C, and D, for example, the predefined series or sequence may be such that the output signals identify transmissions in the frequency ranges C, A, B, D (in this sequence).

A series of transmissions of this type in various frequency ranges is also to be identified in the following as a trigger signal series, because a series of transmissions of this type is to be used for the purpose of triggering the turning on of the transceiver. The sequence of the output signals of the low-power receiver thus always identifies a particular frequency scheme. A frequency scheme is more or less used as a key for turning on the transceiver of a correspondingly preset or programmed implant.

As a supplement or also as a replacement to presetting a sequence, i.e., a frequency scheme, individual times may also be predefined, at which the signals must follow one another. For example, if the sequence is preset as a replacement, the waking unit may solely monitor the time series of signals on only one frequency band.

For the above-mentioned purpose, the low-power receiver preferably has multiple bandpass filters, whose transmission range is tailored to the predefined frequency ranges. A signal detector is assigned to each bandpass filter, which works together with the particular bandpass filter in such a way that the signal detector outputs a signal if the low-power receiver receives a transmission having sufficient signal strength in a particular frequency range which corresponds to the transmission range of the band filter which is assigned to the signal detector. With a low-power receiver of this type, an output signal to be relayed to the waking control unit is provided at the output of a particular signal detector as soon as the low-power receiver receives a transmission of sufficient signal strength in the particular frequency range. In this way, the low-power receiver generates signals or signal sequences which are to be processed further by the waking control unit.

The waking control unit is preferably implemented to detect the sequence of the signals output by the signal detectors and compare it to a predefined sequence, in order to output the waking signal to the transceiver in case of a positive comparison (the received signal sequence corresponds to the predefined sequence).

In addition, the waking control unit may have a time monitoring unit and may be implemented only to generate the waking signal if the signals output by the signal detectors occur one after another within a predefined duration. The predefined duration may be a total duration, within which all signals must occur, and multiple durations may also be predefined, which describe by what time a following signal must follow the particular preceding signal.

In all embodiment variations, an implantable medical device results whose transceiver may be switched from a turned-off or a power saving mode into a turned-on or fully operational mode by receiving a trigger signal sequence, without a signal having to be received at sufficiently good quality to be able to decode the signal for this purpose. Therefore, a simple receiver suffices as the low-power receiver having low energy demand. Nonetheless, targeted response of a correspondingly preset implant is possible, even without corresponding address data in a received signal having to be decoded and analyzed first for this purpose, for example.

A further aspect relates to the reaction of the implant to receiving a trigger signal or a trigger signal sequence. For example, if multiple implants are addressed simultaneously by a trigger signal sequence, this may have the result that all addressed implants simultaneously transmit a response signal to the carrier signal sequence [sic; trigger signal sequence], so that successful communication with an external device is not possible at least for the majority of implants.

To counteract this problem, the implantable medical device preferably has a transmission control unit, which has or is connected to a random generator and is implemented to transmit a response signal after passage of a waiting time after the transceiver is turned on by the waking control unit and, for this purpose, to determine the time of a transmission beginning after the transceiver is turned on by the waking control unit in such a way that the time of the transmission beginning corresponds to the ending time of the waiting time, which in turn begins with the waking signal. The waiting time has a duration which corresponds to the product ZZ×SD of a random number ZZ generated by the random generator and a predetermined, average transmission duration SD.

In this way, the waiting time, after which an implant reacts to a corresponding trigger signal, has a random length, so that it is improbable that two implants will respond to a trigger signal simultaneously.

If, in addition, according to a preferred embodiment variation, the random number is scaled in such a way that it is an integer between 0 and a highest number of implants to be expected in the reception range of an external device minus 1, it is additionally very improbable that a second implant will begin to transmit a response signal during the transmission duration for the transmission of the response signal of a first implant.

In the event of a predefined maximum transmission duration SD to be expected, this duration SD determines a time slot in each case for transmitting the response signal. Because all implants in the surroundings of the external device are waked by the same trigger signal on the part of the external device or—in a more general embodiment—are at least synchronized, the time slots, or the transmission durations SD switched one after another as a function of the particular random number ZZ, are in-phase.

In a scenario of this type, because of the proximity of the implant to the external device, signal runtimes between the implant and the external device are negligible.

For such a scenario, a probability $P_{AI,n}$, that all implants will transmit in different time slots, results for a maximum number of implants AI, predefined for all implants identically, which is larger in any case than the actual number n of the implants, as:

$$P_{AI,n} = P_{AI,n} = \frac{\prod_{i}^{AI} = AI - n + 1^i}{AI^i}.$$

For AI→∞, this probability is $P_{AI,n}1$, i.e., it is very probable for a comparatively large predefined number AI that the implants will each transmit in a separate time slot, i.e., that no two implants will transmit in the same time slot. This is independent of the length of the time slot predefined by the maximum transmission duration SD.

Because the probability that two implants will nonetheless transmit a response signal in the same time slot is close to 0, but is not equal to 0, the transmission control unit is implemented in a preferred embodiment variation for the purpose of repeating the transmission of the response signal after passage of a newly determined waiting time. The repetition of the transmission of the response signal may be a function of whether or not a particular transmitted response signal remains unanswered.

DESCRIPTION OF THE FIGURES

The present invention will be explained in greater detail on the basis of an exemplary embodiment with reference to the figures. In the figures.

DETAILED DESCRIPTION OF THE INVENTION

Figure 1:
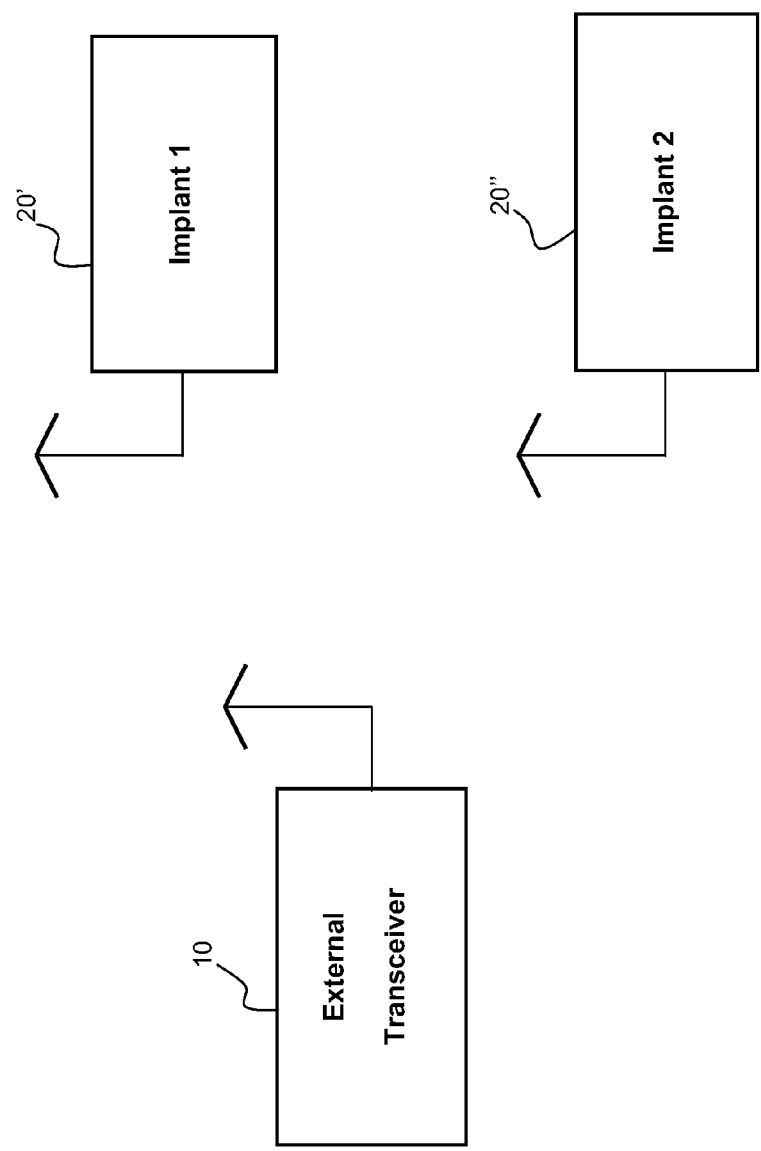
FIG. 1: shows an example of a scenario having an external device and two implants in the range of the external device.

FIG. 1 shows an external device as an external transceiver device 10 and two implants 20' and 20", which are located within a reception range of the external device 10, indicated by a dashed line 12. The reception range results from the transmission power of the implants 20' and 20" and the sensitivity of the receiver of the external device 10.

In connection with the scenario illustrated in FIG. 1, the problem basically results that the implants each have a transceiver 203 (see FIG. 2), which consumes a relatively large amount of energy in the transmission and reception mode and is therefore to be kept as long as possible and as frequently as possible in an energy saving mode, or is to be turned off, but simultaneously is also to be switched into its fully operational mode by a signal from outside the implant. However, as much as possible, this is not to be performed by signals which originate from another implant or completely foreign transmitting device in the reception range of a particular device. If possible, the transceiver 203 of a particular implant is only, as much as possible, to be awoken by an external device like the external device 10.

The problem additionally results from the scenario illustrated in FIG. 1 that both implants 20' and 20" may not wirelessly communicate simultaneously with the external device 10 in the same frequency range.

Figure 2:
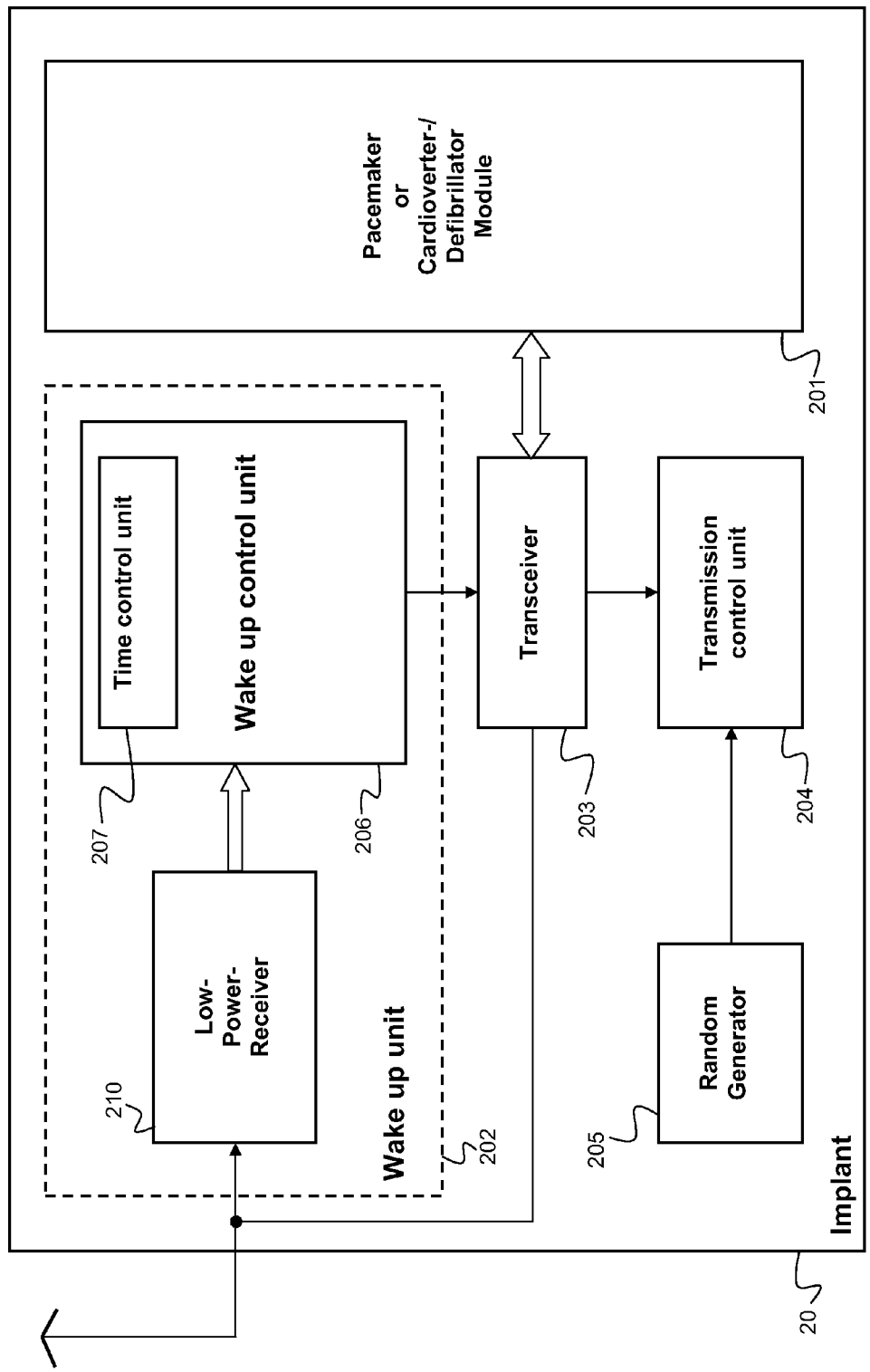
FIG. 2: shows the construction of the transceiver unit of an implant.

The implant 20 shown in FIG. 2 represents a preferred embodiment variation of an implant which deals with both above-mentioned problems.

Firstly, the implant 20 has a waking unit 202, which is connected to the transceiver 203 of the implant 20 and may output a waking signal to the transceiver 203, by which the transceiver 203 may be switched from a turned-off state or an energy saving mode into a fully operational mode, which requires more energy.

The waking signal which the waking unit 202 outputs to the transceiver 203 is to be able to be triggered wirelessly, but not by any arbitrary data transmission. In addition, the reception of a wirelessly transmitted trigger signal which triggers the waking signal is not already to require as much energy as the transceiver 203 requires in its fully operational state.

To achieve this, the waking unit 202 has, in addition to a waking control unit 207, which finally triggers the waking signal, a low-power receiver 210, which is capable as a more wideband receiver of detecting wireless transmissions of signals in various frequency ranges. Concretely, the low-power receiver 210 is capable of detecting transmissions which each exceed a minimal, predefined signal strength in one of multiple predefined frequency ranges and generate an output signal in each case, if it detects a transmission having a signal strength above the predefined minimum in one of the predefined frequency ranges.

Figure 3:
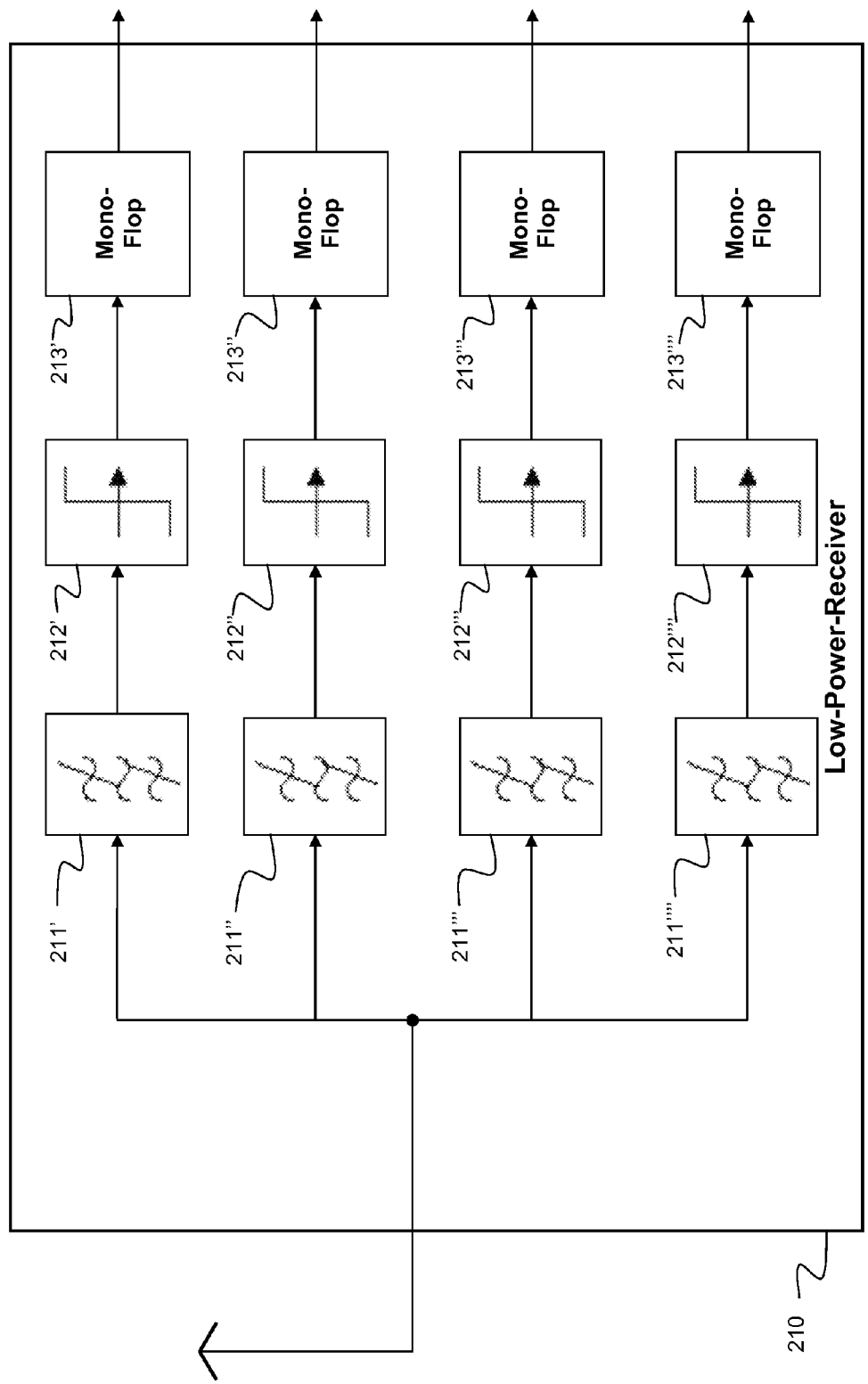
FIG. 3: shows a low-power receiver of the transceiver unit of the implant from FIG. 2.

For this purpose, the low-power receiver (see FIG. 3) has four bandpass filters 211', 211", 211''', and 211'''', each of which has a transmission range (passband), each of which is tuned to one frequency range of a total of four frequency ranges. Each bandpass filter 211', 211", 211''', and 211'''' has a signal detector 212', 213', 212", 213", 212''', 213''', 212'''', 213'''' connected downstream. Each of these signal detectors has a threshold value switch 212', 212", 212''', and 212'''', which responds if an output signal at a signal strength which lies above the predefined threshold is applied to the output of the corresponding assigned bandpass filter 211', 211", 211''', or 211''''. If the particular threshold value switch 212', 212", 212''', or 212'''' accordingly responds to a signal of this type, it triggers a particular monostable flip-flop (monoflop) 213', 213", 213''', or 213'''' connected downstream from the threshold value switch 212', 212", 212''', or 212''''. The particular monostable flip-flop 213', 213", 213''', or 213'''' generates an output signal in this way, which identifies that a transmission of signals having a signal strength above the predefined minimum has occurred in the frequency range predefined via the transmission range of the particular bandpass filter 211', 211", 211''', or 211''''. In this way, the output signals of the monostable flip-flops 213', 213", 213''', and 213'''', which are simultaneously output signals of the low-power transceiver 210, identify by their sequence the sequence with which transmissions in various frequency ranges were received on the part of the low-power receiver 210.

The waking control unit 206 is implemented to analyze the output signals of the low-power receiver 210 in two regards. Firstly, the waking control unit is implemented to compare the sequence of the output signals of the low-power receiver 210 to a predefined sequence and to output the waking signal to the transceiver 203 only if the sequence of the output signals of the low-power receiver 210 corresponds to the predefined sequence stored in the implant 20. In addition, the waking control unit 206 is implemented to ensure with the aid of a time monitoring unit 207 that the waking signal is only generated if the output signals of the low-power receiver 210 not only arrive in the predefined sequence, but rather also in sequence within a particular predefined time.

The predefined sequence of the signals and the corresponding predefined times result in a type of characteristic key, using which, for example, an external device may intentionally wake a transceiver 203 of an implant 20 wirelessly, without data having to be decoded and analyzed for this purpose, which may be contained as address data in a wirelessly transmitted signal, for example.

A transmission control unit 204 of the implant 20 is implemented to controlled the transmission of a response signal which the implant 20 is to transmit after receiving a wirelessly transmitted trigger signal, which has resulted in waking of the transceiver 203 via a corresponding waking signal. The transmission control unit is implemented to first trigger a transmission of the response signal via the transceiver 203 after passage of a waiting time which begins with the waking of the transceiver 203. The transmission control unit 204 calculates this waiting time from a random number ZZ generated by a random generator 205 and a predefined maximum value for a transmission duration SD for the transmission of the response signal B from an also predefined integer AI, which is greater than the maximum number of implants to be expected within the range of an external device.

The waiting time is calculated from the random number ZZ scaled to integers between 0 and AI-1, and the predefined maximum transmission duration SD stored in the implant, as the product of the integral random number ZZ, which is scaled by AI, and SD: ZZ×SD.

The particular waiting time defined in this way is started with reception of the carrier signal [sic; trigger signal] and results in the control unit 204 triggering the transmission of the response signal via the receiver 203 at the end of the waiting time.

As already explained, it is extremely improbable that more than one implant in the range of an external device will simultaneously respond to a trigger signal transmitted by the external device if SD is greater than the transmission time for the transmission of the response signal and if AI is greater than the maximum number of implants which are located within the range (indicated in FIG. 1 by the dashed line 12) of the external device 10.

This effectively avoids two implants responding simultaneously to a trigger signal.

What is claimed is:

1. An implantable medical device (20) comprising:
    a transceiver (203) that comprises a first transmitter and first receiver configured to transmit and receive wirelessly transmitted data respectively, wherein said transceiver is turned off or switched into an energy-saving rest state between individual data transmissions
    a waking unit (202), which is configured to switch said transceiver (203) from its turned-off state or its rest state into its fully operational state by a waking signal;
    wherein said waking unit comprises
        a second receiver independent of said first receiver wherein said second receiver is a low-power receiver (210) that requires less energy as said transceiver in said transceiver's fully operational state and
        a waking control unit (206), of which said low-power receiver (210) is configured to monitor multiple predefined frequency ranges in such a way that, in case of a transmission of sufficient signal strength in one or more frequency ranges said low-power receiver (210) generates an output signal and outputs said output signal to said waking control unit (206), and of which said waking control unit (206) is configured to analyze output signals of said low-power receiver (210) and to output said waking signal to said transceiver (203), which switches said transceiver (203) on or to fully operational, if a predefined condition is met or multiple predefined conditions are met;
    wherein said waking control unit (206) is configured to output said waking signal to said transceiver (203) if a condition is met that said low-power receiver (210) outputs a sequence of output signals which identify that said low-power receiver (210) has detected a series of data transmissions of sufficient signal strength in various frequency ranges which correspond to a predefined series/sequence of frequencies; and,
    a transmission control unit (204), wherein said transmission control unit (204) has or is connected to a random generator (205) and is configured, after lapse of a waiting time after said transceiver (203) is turned on by said waking control unit (206), to transmit a response signal and to define a time of a transmission beginning after said transceiver (203) is turned on by said waking control unit (206) for this purpose in such a way that said time of said transmission beginning corresponds to an ending time of said waiting time, which begins with said waking signal and has a duration which corresponds to a product ZZ·SD of a random number ZZ generated by said random generator (205) and at least one predetermined average transmission duration SD.

2. The implantable medical device (20) according to claim 1, wherein said low-power receiver (210) has multiple bandpass filters (211', 211", 211''', 211''''), each having an assigned signal detector (212', 212", 212''', 212''''), which work together in such a way that a particular signal detector (212', 212", 212''', 212'''') outputs a signal if said low-power receiver (210) receives a transmission having sufficient signal strength in a particular frequency range which corresponds to a transmission range or passband of said bandpass filters (211', 211", 211''', 211'''') which is assigned to said particular signal detector (212', 212", 212''', 212'''').

3. The implantable medical device (20) according to claim 2, wherein said waking control unit (206) is configured to detect a sequence of signals output by signal detectors (212', 212", 212''', 212'''') and compare said sequence of signal to a predefined sequence and output said waking signal to said transceiver (203) in case of a positive comparison.

4. The implantable medical device (20) according to claim 3, wherein said waking control unit (206) has a time monitoring unit (207) and is configured to generate said waking signal only if signals output by said signal detectors (212', 212", 212''', 212'''') occur in sequence within a predefined duration.

5. The implantable medical device (20) according to claim 1, wherein said transmission control unit (204) is configured to scale said random number ZZ in such a way that said random number ZZ is an integer between 0 and a predefined maximum number of implantable medical devices (20', 20") located in reception range of an external device (10) minus one.

6. The implantable medical device (20) according to claim 1, wherein said transmission control unit (204) is configured to repeat a transmission of said response signal after passage of a newly determined waiting time.

7. The implantable medical device (20) according to claim 1 wherein said implantable medical device (20) is a cardiac pacemaker or a cardioverter/defibrillator or a combination of both.

8. An implantable medical device (20) comprising:
 a transceiver (203) that comprises a first transmitter and first receiver configured to transmit and receive wirelessly transmitted data respectively, wherein said transceiver is turned off or switched into an energy-saving rest state between individual data transmissions;
 a waking unit (202), which is configured to switch said transceiver (203) from its turned-off state or its rest state into its fully operational state by a waking signal;
 wherein said waking unit comprises
  a second receiver independent of said first receiver wherein said second receiver is a low-power receiver (210) that requires less energy as said transceiver in said transceiver's fully operational state and
  a waking control unit (206), of which said low-power receiver (210) is configured to monitor multiple predefined frequency ranges in such a way that, in case of a transmission of sufficient signal strength in one or more frequency ranges said low-power receiver (210) generates an output signal and outputs said output signal to said waking control unit (206), and of which said waking control unit (206) is configured to analyze output signals of said low-power receiver (210) and to output said waking signal to said transceiver (203), which switches said transceiver (203) on or to fully operational, if a predefined condition is met or multiple predefined conditions are met;
 wherein said waking control unit (206) is configured to output said waking signal to said transceiver (203) if a condition is met that said low-power receiver (210) outputs a sequence of output signals which identify that said low-power receiver (210) has detected a series of data transmissions of sufficient signal strength in various frequency ranges which correspond to a predefined series/sequence of frequencies;
 wherein said low-power receiver (210) has multiple bandpass filters (211', 211", 211''', 211''''), each having an assigned signal detector (212', 212", 212''', 212''''), which work together in such a way that a particular signal detector (212', 212", 212''', 212'''') outputs a signal if said low-power receiver (210) receives a transmission having sufficient signal strength in a particular frequency range which corresponds to a transmission range, or passband, of said bandpass filters (211', 211", 211''', 211'''') which is assigned to said particular signal detector (212', 212", 212''', 212'''');
 wherein said waking control unit (206) is configured to detect a sequence of signals output by signal detectors (212', 212", 212''', 212'''') and compare said sequence of signal to a predefined sequence and output said waking signal to said transceiver (203) in case of a positive comparison;
 wherein said waking control unit (206) has a time monitoring unit (207) and is configured to generate said waking signal only if signals output by said signal detectors (212', 212", 212''', 212'''') occur in sequence within a predefined duration; and,
 a transmission control unit (204), wherein said transmission control unit (204) has or is connected to a random generator (205) and is configured, after lapse of a waiting time after said transceiver (203) is turned on by said waking control unit (206), to transmit a response signal and to define a time of a transmission beginning after said transceiver (203) is turned on by said waking control unit (206) for this purpose in such a way that said time of said transmission beginning corresponds to an ending time of said waiting time, which begins with said waking signal and has a duration which corresponds to a product ZZ·SD of a random number ZZ generated by said random generator (205) and at least one predetermined average transmission duration SD.

9. The implantable medical device (20) according to claim 8, wherein said transmission control unit (204) is configured to scale said random number ZZ in such a way that said random number ZZ is an integer between 0 and a predefined maximum number of implantable medical devices (20', 20") located in reception range of an external device (10) minus one.

10. The implantable medical device (20) according to claim 8, wherein said transmission control unit (204) is configured to repeat a transmission of said response signal after passage of a newly determined waiting time.

11. The implantable medical device (20) according to claim 8 wherein said implantable medical device (20) is a cardiac pacemaker or a cardioverter/defibrillator or a combination of both.

* * * * *